United States Patent
Crawley

[11] Patent Number: 5,919,969
[45] Date of Patent: Jul. 6, 1999

[54] SYNTHESIS OF YELLOW COUPLERS

[75] Inventor: Michael W. Crawley, Kingswood, United Kingdom

[73] Assignee: Eastman Kodak Company, Rochester, N.Y.

[21] Appl. No.: 08/868,654

[22] Filed: Jun. 4, 1997

[30] Foreign Application Priority Data

Jun. 5, 1996 [GB] United Kingdom ............... 9611687

[51] Int. Cl.[6] .............................................. C07C 229/00
[52] U.S. Cl. ........................ 560/43; 560/147; 560/180; 560/171
[58] Field of Search .................... 560/43, 147, 171, 560/180

[56] References Cited

FOREIGN PATENT DOCUMENTS 07281373 10/1995 Japan .

*Primary Examiner*—Paul J. Killos
*Attorney, Agent, or Firm*—Arthur E. Kluegel

[57] ABSTRACT

The invention provides a method of synthesis of a image-dye forming coupler of formula (I)

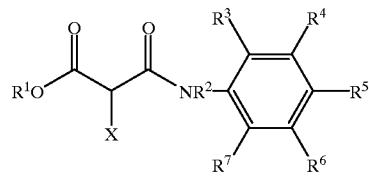

(I)

wherein X is a substituent linked to the coupler by an atom of oxygen, sulfur or nitrogen $R^1$ is an alkyl or aryl group, $R^2$ is a hydrogen atom or an alkyl group; $R^3$ to $R^7$ are the same or different and selected from a hydrogen atom and substituent groups;

which method comprises the reaction of a compound of formula (II)

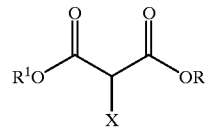

(II)

wherein R and $R^1$ are the same or different and are as defined above for $R^1$ and X is as defined above with a compound of formula (III)

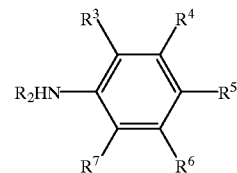

(III)

wherein $R^2$ to $R^7$ are as defined above, in the presence of an inert organic solvent.

17 Claims, No Drawings

SYNTHESIS OF YELLOW COUPLERS

FIELD OF THE INVENTION

The present invention relates to the synthesis of certain acylacetanilide compounds.

BACKGROUND OF THE INVENTION

Photographic layers sensitive to blue light for use in color photographic materials typically contain a yellow coupler which, on reaction with an oxidized arylamine developer, forms a yellow dye. Most commercially available photographic films contain pivaloyl- or benzoylacetanilide yellow couplers. These classes of couplers are, in general, satisfactory, but a person skilled in the art will be aware that even the best examples of these classes are a compromise between coupler activity on the one hand and dye stability on the other. Dodecyl 4-chloro-3-[2-(1-benzyl-5-ethoxy-2,4-dioxoimidazol-3-yl)-2-(2,2-dimethylpropanoyl)-acetamido]benzoate, for example, has good dye stability, but has a relatively poor contrast; dodecyl 4-chloro-3-[2-(1-benzyl-5-ethoxy-2,4-dioxoimidazolin-3-yl)-2-(4-methoxybenzoyl)acetamido]benzoate, on the other hand, has a relatively good contrast but poor dye stability. There has therefore been a requirement to find further classes of yellow couplers. In each class discovered there is a chance that one or more examples may exhibit a combination of parameters which is better than the yellow couplers hitherto available in the prior art.

UK patent application Nos. 9513108.2 and 9513114.0 respectively disclose further classes of yellow dye-forming couplers, namely thenoylacetamides and pyrroloylacetamides, which can have properties which are at least comparable to the commercially available couplers in terms of coupler activity, contrast and/or light and dark/wet fade properties.

A further class of yellow dye-forming couplers is disclosed in U.S. Pat. No. 5,338,654 and U.S. Pat. No. 2,500,487 which disclose certain malonic acid half ester, half amides, which are useful as photographic couplers, providing yellow image dyes with good stability and having excellent dye characteristics such as high color density and sharpness.

A single method for preparing these couplers is disclosed therein which involves the addition of the required coupling-off group to the halogenated half ester, half amide in a yield of 70–80%. However there is no disclosure of the preparation of the starting material for this reaction. Attempts to prepare the halogenated couplers of this type by a number of standard methods used for the synthesis of conventional acylacetanilide couplers have failed to produce pure samples of the chloro or bromo couplers. Extensive quantities of starting material and dichloro or dibromo couplers were formed in all cases which made the ensuing metathesis of halogen for the coupling-off group very difficult to carry out.

PROBLEM TO BE SOLVED BY THE INVENTION

There is therefore a need to find a method of preparation of malonic half amide, half esters which provides the product by a simple route in good yield without the formation of undue by-products.

SUMMARY OF THE INVENTION

According to the present invention therefore there is provided a method of synthesis of an image dye-forming coupler compound of formula (I)

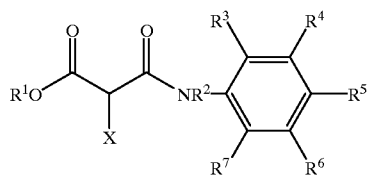

(I)

wherein X is a coupling-off group, $R^1$ is an alkyl or aryl group, each of which is unsubstituted or substituted with one or more coupler-modifying groups, or a 5–10 membered heterocyclic group containing one or more heteroatoms selected from N, O and S, said heterocyclic ring being unsubstituted or substituted with one or more coupler-modifying groups; $R^2$ is a hydrogen atom or an alkyl group which is unsubstituted or substituted with one or more coupler-modifying groups; $R^3$ to $R^7$ are the same or different and selected from a hydrogen atom and coupler-modifying functional groups; which comprises the reaction of a compound of formula (II)

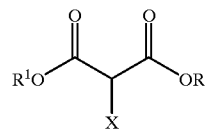

(II)

wherein R and $R^1$ are the same or different, preferably the same, and are as defined above for $R^1$ and X is as defined above with a compound of formula (III)

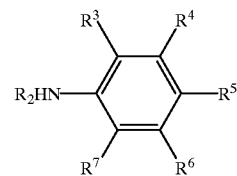

(III)

wherein $R^2$ to $R^7$ are as defined above, in the presence of an inert organic solvent.

According to a further aspect of the invention there is provided a method of preparing the intermediate of formula (II) which comprises the reaction of a compound of formula (IV)

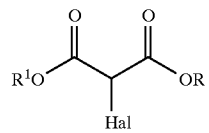

(IV)

wherein R and $R^1$ are as hereinbeforedefined and Hal is a halogen atom, with a compound XH, where X is as hereinbeforedefined, in a solvent in the presence of a base.

According to yet a further aspect of the invention there is provided a novel image dye-forming coupler of formula (I)'

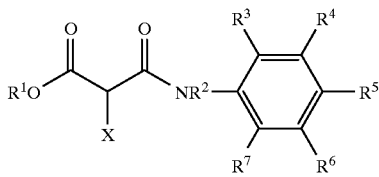

(I)' wherein $R^1$ is an unbranched alkyl group which is unsubstituted or substituted with one or more coupler-modifying groups, other than alkyl groups, and $R^2$–$R^7$ and X are as defined above for a coupler of formula (I).

In yet another aspect the invention provides a photographic element containing an image dye-forming coupler of formula (I)', in association with a light-sensitive silver halide emulsion layer.

There is also provided according to the invention a multi-color photographic material comprising a support bearing yellow, magenta and cyan image dye-forming units comprising at least one blue-, green-, or red-sensitive silver halide emulsion layer having associated therewith at least one yellow, magenta or cyan dye-forming coupler respectively, wherein at least one dye-forming coupler is a coupler of formula (I)' as hereinbefore defined.

ADVANTAGEOUS EFFECT OF INVENTION

An improved method is provided for the synthesis of malonic acid half ester, half amides which are useful as yellow photographic couplers. Couplers can be prepared in a good yield from an intermediate which is readily prepared and without significant concomitant halogenated side-products.

DETAILED DESCRIPTION OF THE INVENTION

The invention has been described in detail with particular reference to certain preferred embodiments thereof, but it will be understood that variations and modifications can be effected within the spirit and scope of the invention.

The reactions take place according to the following sequence:

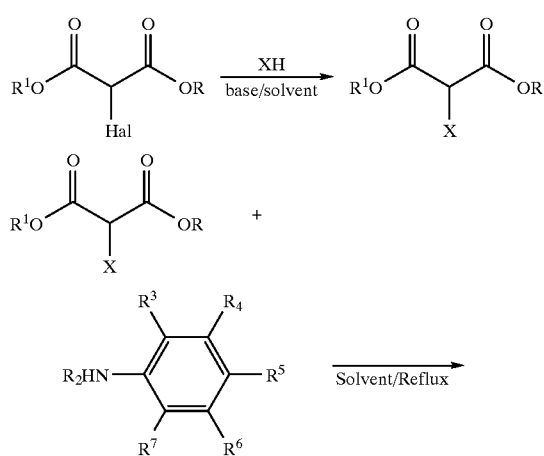

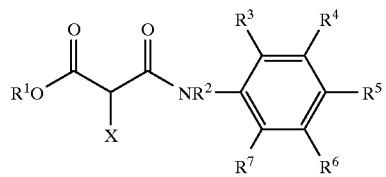

-continued wherein R, $R^1$–$R^7$ and X are as herein before defined.

The final reaction step is preferably carried out in a solvent which has a boiling point between 60° and 200°, especially a non-aprotic solvent which is a hydrocarbon or a high-boiling ether. Most preferably the solvent is benzene, o-dichlorobenzene, diphenyl ether or especially toluene or xylene. The reaction is typically carried out at the boiling point of the chosen solvent.

For the previous step in which the intermediate is prepared preferred solvents are acetonitrile, sulpholane, dimethylfomamide, dimethylacetamide, tetrahydrofuran or dimethylsulfoxide, most preferably acetonitrile. Either an organic or an inorganic base may be used but organic bases are preferred and in particular tertiary amines such as triethylamine, diisopropylethylamine and dimethylaniline; or pyridine or, most preferably, tetramethylguanidine. The reaction can be carried out at temperatures ranging from 0°–100°, but most preferably and conveniently at 20° (room temperature).

In the above formulae the substituents are sufficiently lipophilic, either singly or in combination, so as to render the coupler immobile in a photographic material.

The coupling-off group is a group adapted to be split off from the coupler as a result of reaction between the coupler and the oxidation product of an arylamine color developer. A coupler-modifying group is a substituent which, by its presence in the coupler structure, influences the photographic or physical properties of the coupler or the dye derived from the coupler and may, for example be a coupler-solubilising group, a ballasting group or a dye-hue modifying group.

In the coupler of formula (I) typically $R^1$ may be selected from alkyl, aryl or heterocyclic optionally substituted, for example, with one or more halo, alkyl, aryl, alkoxy or aryloxy groups, which, with the exception of halo, may themselves in turn be so substituted. Preferably $R^1$ may be alkyl, phenyl, naphthyl or pyridyl, most preferably alkyl, and in particular may be selected from the groups below, without limitation thereto.

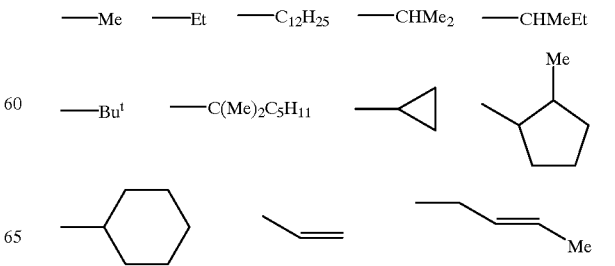

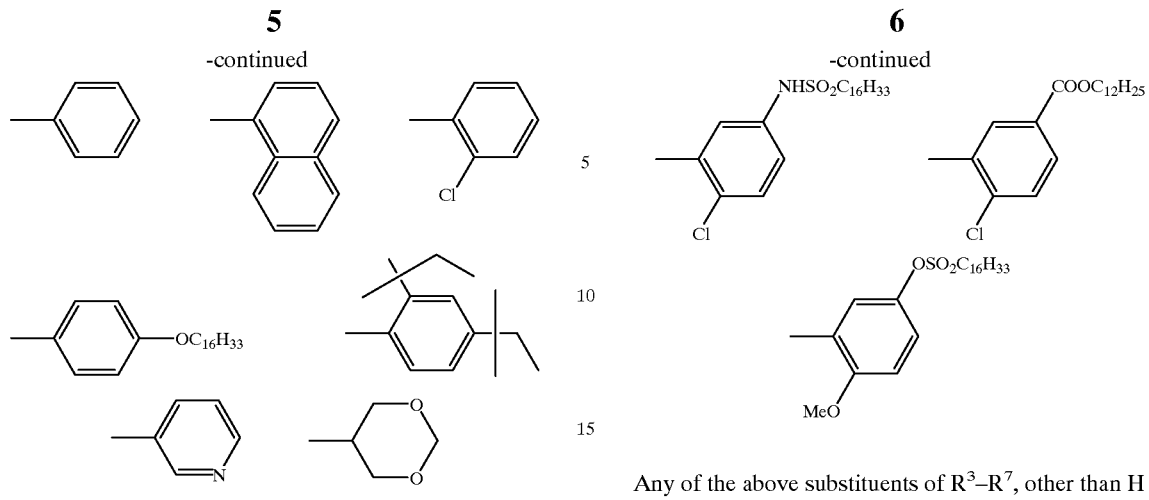

$R^2$ is preferably an unsubstituted alkyl group or more preferably a hydrogen atom. $R^3-R^7$ may be any substituent that is not deleterious to the coupling reaction between the coupler and oxidized developer. Examples of the substituents are, but not limited to, H, halogen, $R^1$, $R^1O$, $R^1_2N$, $R^1HN$, $H_2N$, $R^1S$, $R^1SO$, $R^1SO_2NH$, $R^1SO_2$, $R^1SO_2O$, $R^1OOC$, HOOC, $R^1COO$, $R^1NHCO$, $R^1_2NCO$, $R^1NHCONH$, $R^1CONH$, $R^1NHSO_2$, $R^1_2NSO_2$, $H_2NSO_2$, $R^1CO$, $NO_2$, CN, $CF_3$, $P(OR^1)_3$, $PO(OR^1)_3$, where $R^1$ has the above meaning. Substituents $R^3$ and $R^4$, $R^4$ and $R^5$, $R^5$ and $R^6$ and/or $R^6$ and $R^7$ may represent fused cyclic groups (e.g. $R^3$ and $R^4$ may represent the residue of a fused benzene or pyridine ring). Preferably the phenyl ring is ortho-substituted, particularly with a chloro group, although an additional substituent in the meta- or para-position may advantageously be present.

Some representative examples of the substituted aryl group within the anilide portion of the coupler of formula (I) are as follows, but are not limited thereto.

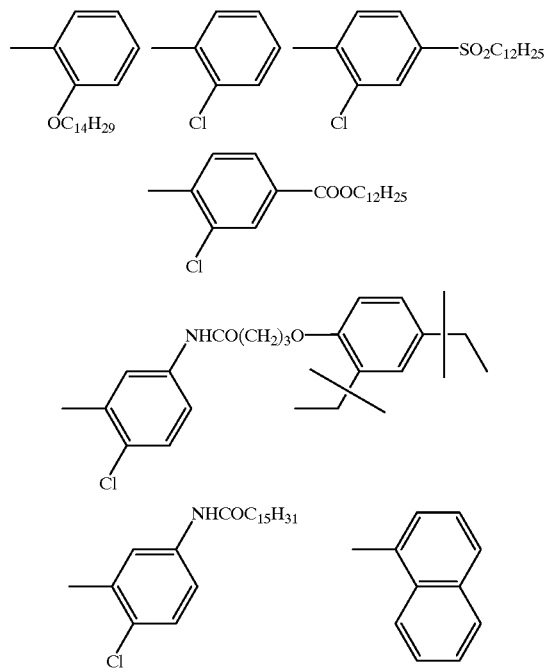

Any of the above substituents of $R^3-R^7$, other than H and halogen, may further be substituted with one or more of the same or different substituents of $R^3-R^7$ as hereinbeforedefined.

As used herein and throughout the specification the term alkyl refers to an unsaturated or saturated straight or branched chain alkyl group having 1–20 atoms and includes cycloalkyl having 3–8 carbon atoms.

It will be appreciated that X may be any coupling-off group known to a person skilled in the linked to the molecule by an atom of oxygen, sulfur or nitrogen. The released moiety may or may not have properties which affect the photographic process. For instance the released moiety may be a competing coupler, a silver development inhibitor or a silver bleaching accelerating agent etc. The coupling-off group may also be a chemical switch which will release a photographically useful agent in a controlled, timed, image-wise fashion.

X may be selected from acyloxy, sulfonyloxy, aryloxy, phosphonyloxy, azo groups, sulphonamides, heteroaryloxy, alkylthio, arylthio, heteroarylthio and n-heterocycles (attached to the coupling site by the heteroatom), such as urethane, imido, 2,4-oxazolidinedione, pyridone, pyridazone, phthalimido, succinimido, hydantoinyl, triazole, triazoledione, tetrazole, imidazole, pyrazole and benzotriazole.

Any of the above substituents, may be substituted with one or more substituents $R^3-R^7$ as hereinbefore defined. Representative examples of the coupling-off group X are shown below but are not limited thereto.

SCN, OMe, OPh, $NHSO_2Me$, OCOMe, $OSO_2Ph$, $OPO(OEt)_2$, $SCH_2CH_2COOH$

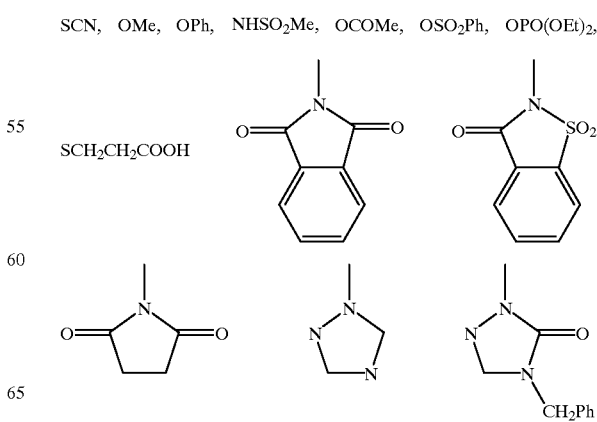

-continued

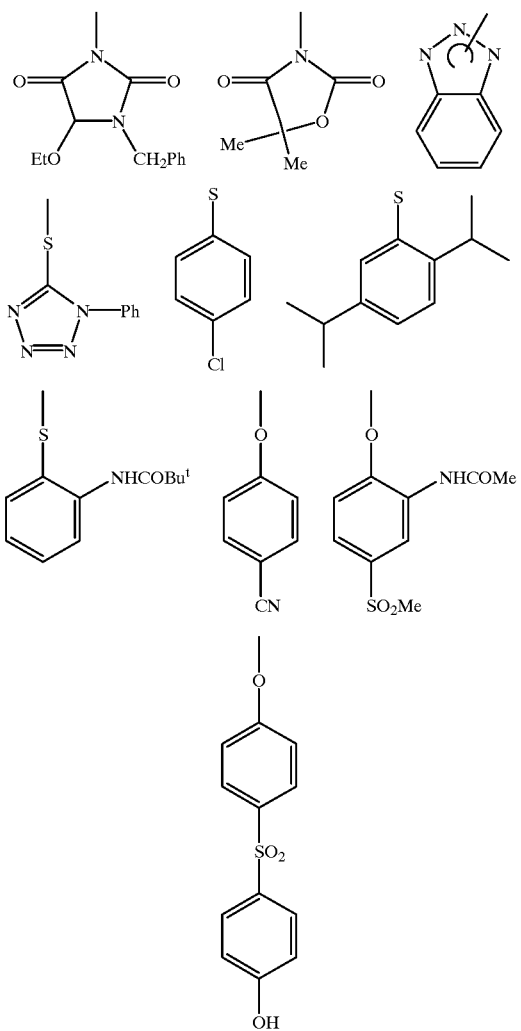

The couplers prepared by the present invention preferably contain a photographic ballast group in one of the groups $R^1$, $R^2$, $R^3$–$R^7$ or X. Photographic ballast groups are known in the art and described as an organic group of such size and configuration as to make the coupler non-diffusible in a coated photographic element. Two or more couplers may be attached to the same ballast molecule.

Unless otherwise specifically stated, when a substituent group contains a substitutable hydrogen, it is intended to encompass not only the substituent's unsubstituted form, but also its form further substituted with any group or groups as herein mentioned, so long as the group does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy)propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methyl-sulfonamido, benzenesulfonamido, p-toluylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, sush as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecyl-amidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

Couplers of formula (I) are capable of providing dyes with hue characteristics comparable to those obtained from other yellow couplers in current use. In particular the dyes have low secondary absorptions in the green and red regions of the spectrum, narrow half-bandwidth and good light and thermal stability. The couplers themselves have good raw stock keeping properties and low continued coupling characteristics and are readily prepared from inexpensive precursors in a short number of steps giving advantages in the cost of manufacture.

In some embodiments, the image dye-forming coupler may be selected from the following couplers but are in no way limited thereto:

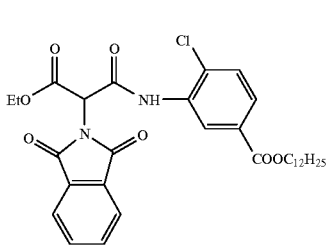

-continued (C11) (C12) (C13) (C14) (C15) (C16) (C17) (C18) (C19) (C20) (C21) (C22) (C23) (C24)

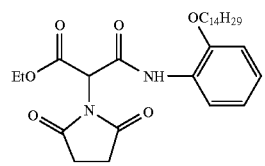 (C25)
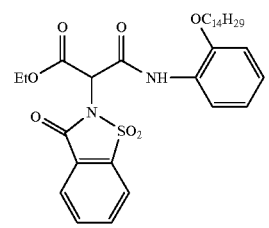 (C26)
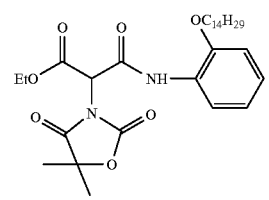 (C27)
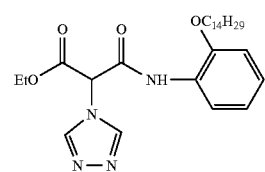 (C28)
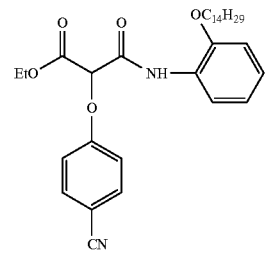 (C29)
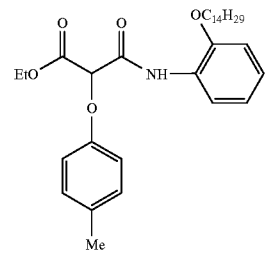 (C30)
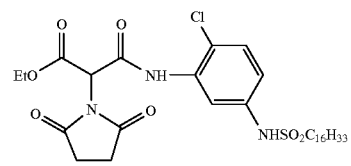 (C31)
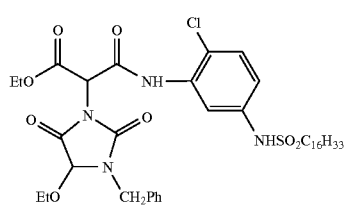 (C32)
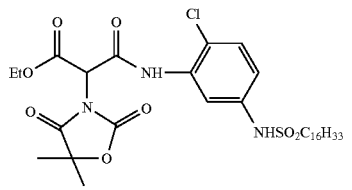 (C33)
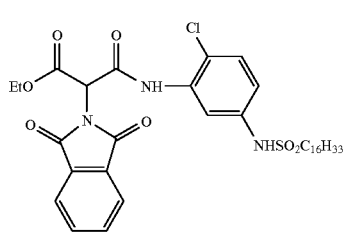 (C34)
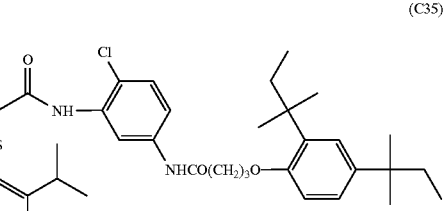 (C35)
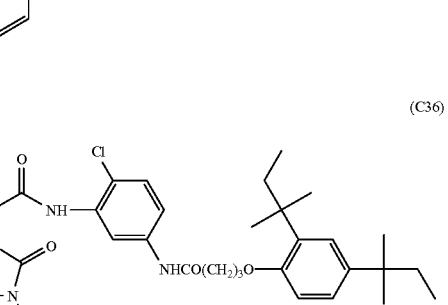 (C36)
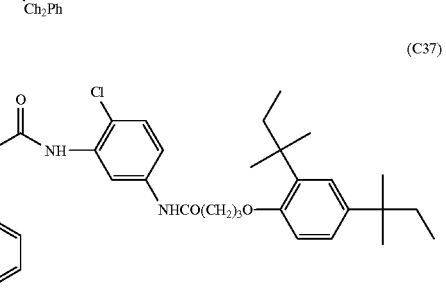 (C37)

-continued (C38)
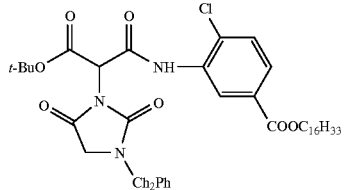

(C39)
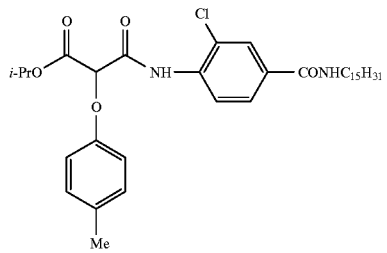

(C40)
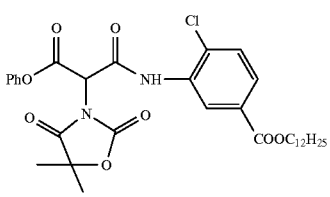

(C41)
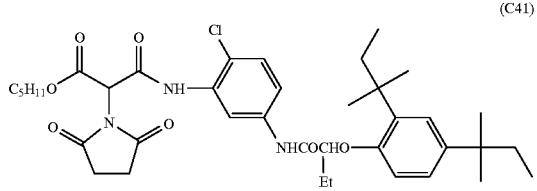

(C42)
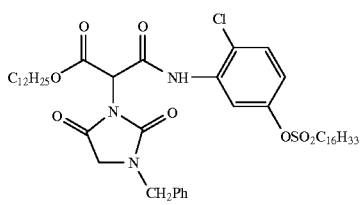

Control Couplers:

(CC1)
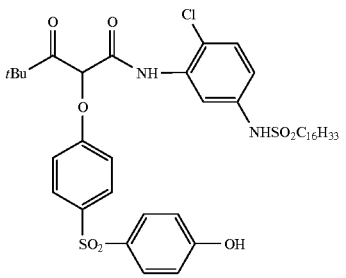

-continued (CC2)
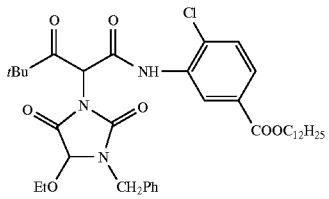

The photographic element may be a single color element or a multicolor element. Multicolor elements contain image dye-forming units sensitive to each of the three primary regions of the visible range of the electromagnetic spectrum. Each unit may comprise a single emulsion layer or a plurality of emulsion layers sensitive to a given region of the spectrum. The layers of the element, including the layers of the image dye-forming units, may be arranged in various orders as known in the art. In an alternative format, the emulsions sensitive to each of the three primary regions of the spectrum may be disposed as a single segmented layer.

A typical multicolor photographic element comprises a support bearing a cyan image dye-forming unit comprising a red-sensitive silver halide emulsion layer and a cyan dye-forming coupler; a magenta image dye-forming unit comprising at least one green-sensitive silver halide emulsion layer and a magenta dye-forming coupler; a yellow image dye-forming unit comprising at least one blue-sensitive silver halide emulsion layer and a yellow dye-forming coupler. The element may contain additional layers, such for example as filter layers, interlayers, overcoat layers and subbing layers.

If desired, the photographic element can be used in conjunction with an applied magnetic layer as described in *Research Disclosure,* November 1992, Item 34390 published by Kenneth Mason Publications, Ltd., Dudley Annex, 12a North Street, Emsworth, Hampshire PO10 7DQ, England, the contents of which are incorporated herein by reference. When it is desired to (employ the inventive materials in a small format film, *Research Disclosure,* June 1994, Item 36230, provides suitable embodiments.

In the following discussion of suitable materials for use in the emulsions and elements of this invention, reference will be made to *Research Disclosure*, September 1994, item 36544, available as described above, which will be identified hereafter by the term "Research Disclosure". The contents of the Research Disclosure, including the patents and publications referenced therein, are incorporated herein by reference and the Sections hereafter referred to are Sections of the Research Disclosure.

The silver halide emulsions employed in the elements of this invention can be either negative-working or positive-working. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through IX. Color materials are described in Sections X through XIII. Scan facilitating is described in Section XIV. Supports, exposure, development systems, and processing methods and agents are described in Sections XV to XX. Certain desirable photographic elements and processing steps are described in Research Disclosure, Item 37038, February 1995.

With negative working silver halide a negative image may be formed. Optionally a positive (or reversal) image may be formed.

The color developing agent may be selected from p-phenylenediamines; typically the agent may be selected from: 4-amino-N,N-diethylaniline hydrochloride, 4-amino-3-methyl-N,N-diethylaniline hydrochloride, 4-amino-3-methyl-N-ethyl-N-(2-methanesulfonamido-ethyl)aniline sesquisulfate hydrate, 4-amino-3-methyl-N-ethyl-N-(2-hydroxyethyl)aniline sulfate, 4-amino-3-(2-methanesulfonamido ethyl)-N,N-diethyl-aniline hydrochloride and 4-amino-N-ethyl-N-(2-methoxyethyl)-m-toluidine di-p-toluene sulfonic acid.

The yellow coupler prepared in accordance with the invention may be used in combination with other classes of image couplers such as 3-acylamino and 3-anilino-5-pyrazolones and heterocyclic couplers (e.g. pyrazoloazoles) such as, for example, those described in EP 285,274, U.S. Pat. No. 4,540,654 and EP 119,860; and other 5-pyrazolone couplers containing different ballasts or coupling-off groups such as, for example, those described in U.S. Pat. No. 4,301,235, U.S. Pat. No. 4,853,319 and U.S. Pat. No. 4,351,897. Yellow or cyan colored couplers (e.g. to adjust levels of interlayer correction) and/or masking couplers such as, for example, those described in EP 213,490, Japanese Published Application 58-172,647, U.S. Pat. No. 2,983,608, German Application DE 2,706, 117C, U.K. Patent 1,530,272, Japanese Application A-113935, U.S. Pat. No. 4,070,191 and German Application DE 2,643,965 may also be used. Said masking couplers may be shifted or blocked.

Photographically useful coupling-off groups are well-known in the art. Such groups can determine the equivalency of the coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, development acceleration or inhibition, bleach acceleration or inhibition, electron transfer facilitation and color correction.

Representative classes of coupling-off groups include halo, alkoxy, aryloxy, heteryloxy, sulfonyloxy, acyloxy, acyl, heterocyclyl, sulfonamido, mercaptotetrazole, mercaptopropionic acid, phosphonyloxy, arylthio, and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in U.K. Patents and published application Nos. 1,466,728, 1,531,927, 1,533,039, 2,006,755A and 2,017,704A, the disclosure of which are incorporated herein by reference.

Thus, a coupler prepared by the present invention may be used in association with materials that accelerate or otherwise modify the processing steps e.g. of bleaching or fixing to improve the quality of the image. Bleach accelerators described in EP 193,389; EP 301,477; U.S. Pat. No. 4,163,669; U.S. Pat. No. 4,865,956; and U.S. Pat. No. 4,923,784 are particularly useful. Also contemplated is use of the coupler in association with nucleating agents, development accelerators or their precursors (U.K. Patent 2,097,140; U.K. Patent 2,131,188; electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The yellow coupler may be used in combination with filter dye layers comprising colloidal silver sol or yellow and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543,323). Also, the couplers may in some embodiments be blocked or coated in protected form as described, for example, in Japanese Application 61/258,249 or U.S. Pat. No. 5,019,492.

The yellow coupler may further be used in combination with image-modifying compounds such as "Developer-Inhibitor-Releasing" compounds (DIR's); DIR's useful in conjunction with said couplers are known in the art and examples are described in U.S. Pat. Nos. 3,137,578; 3,148,022; 3,148,062; 3,227,554; 3,384,657; 3,379,529; 3,615,506; 3,617,291; 3,620,746; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346,899; 362,870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography", C. R. Barr. J. R. Thirtle and P. W. Vittum in Photographic Science and Engineering, Vol. 13, p.174 (1969), incorporated herein by reference.

Generally, the developer inhibitor-releasing (DIR) couplers may include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thia-diazoles, oxathiazoles, thiatriazoles, benzotriazoles, tetrazoles, benzimidazoles, indazoles, isoindazoles, mercaptotetrazoles, selenotetrazoles, mercaptobenzo-thiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptothiatriazoles, mercaptooxadiazoles, mercaptodiazoles, mercaptooxathiazoles, tellurotetrazoles or benzisodiazoles.

The invention will now be described with reference to the following examples but is in no way to be construed as limited thereto.

All the starting materials are readily available or can be prepared according to standard methods well known in the art. All the products described gave satisfactory proton NMR spectra, Mass spectra, Infra-red spectra and Microanalytical data.

EXAMPLE 1

Preparation of Coupler (C13)

Ethyl N-(2-chloro-4-dodecylsulphonylphenyl)-2-phthalimidomalonamate

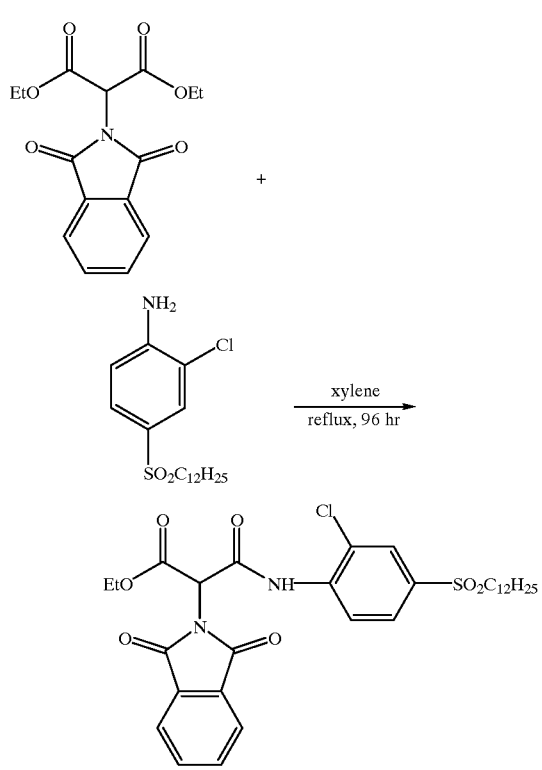

Diethyl 2-phthalimidomalonate (obtained from Aldrich Chemical Company Limited) (9.8 g, 32.0 mmol) and 2-chloro-4-dodecylsulphonylaniline (11.5 g, 32.0 mmol) were added to xylene (250 ml) and refluxed under a Dean and Stark trap for 96 hr. The distillate was periodically removed and the main bulk of solvent replenished as necessary. Removal of the xylene solvent under reduced pressure afforded a light brown oil which was purified by column chromatography using a 4:1 mixture of 60–80° C. petroleum ether:ethyl acetate and silica gel. The product, coupler (C13), was obtained as a white solid which was slurried with a little petroleum ether, filtered and dried in air, 13.6 g, 67%.

| $C_{31}H_{39}ClN_2O_7S$ | Requires: C 60.1%; H 6.35%; N 4.5% |
| --- | --- |
| | Found: C 60.0%; H 6.3%; N 4.6% |

EXAMPLE 2

Preparation of Coupler (C21)

(a) Diethyl 2-(3-benzyl-2,5-dioxo-1,3-diazolidin-1-yl)malonate

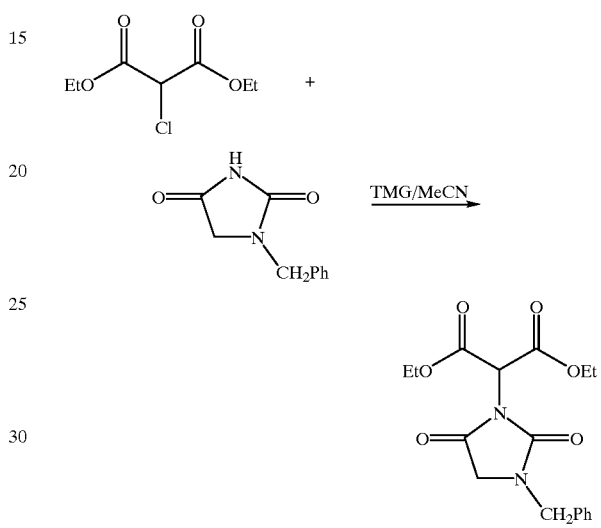

1-Benzyl-2,4-imidazolindione (19.0 g, 100 mmol) was suspended in acetonitrile (80 ml) and stirred at room temperature. Diethyl chloromalonate (19.5 g, 100 mmol) was added followed by the dropwise addition of tetramethylguanidine (23.0 g, 200 mmol). The mixture was stirred for 12 hr. Thin layer chromatographic analysis (1:1 ethyl acetate:60–80° C. petroleum ether;silica gel) indicated traces of starting materials, one major (Rf=0.75) and one minor component (Rf=0.8). The mixture was poured into dilute (1N) hydrochloric acid and the resulting oil extracted into ethyl acetate, washed and dried ($MgSO_4$). Removal of the solvent and addition of 1:1 ethyl acetate:60–80° C. petroleum ether (50 ml) gave a small amount of 1-benzyl-2,4-imidazolindione (3.35 g, 18% recovery) which was filtered off washed with petroleum ether and dried in air. The filtrate was chromatographed using 1:1 ethyl acetate: 60–80° C. petroleum ether as eluent on silica gel. The minor component was eluted first and identified as a 6:1 mixture of tetraethyl ethylene tetracarboxylate oxide and tetraethyl ethylenetetracarboxylate (0.5 g). The major component, was then eluted and the solvent removed under reduced pressure to give diethyl 2-(3-benzyl-2,5-dioxo-1-imidazolinyl) malonate (21.0 g, 60%) as a clear viscous oil.

(b) Preparation of Coupler (C21)

Ethyl N-(2-tetradecyloxylphenyl)-2-(3-benzyl-2,5-dioxo-1,3-diazolidin-1-yl)malonamate

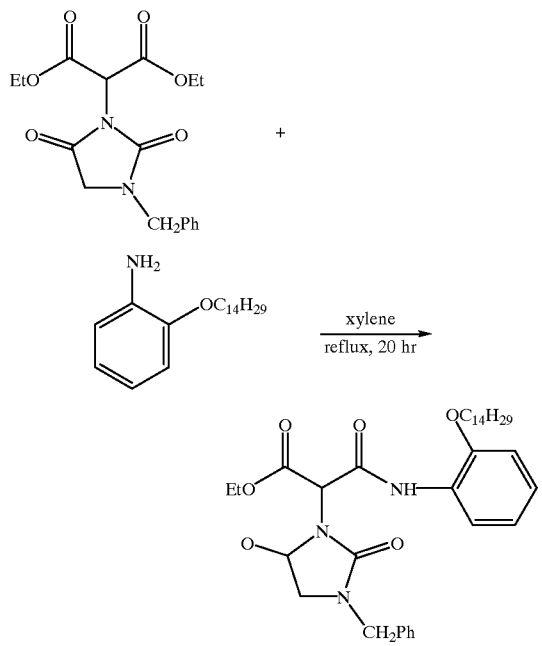

Diethyl 2-(3-benzyl-2,5-dioxo-1-imidazolinyl)malonate (18.0 g, 52.0 mmol) and 2-tetradecyloxyaniline (15.8 g, 52 mmol) were dissolved in xylene (200 ml) and heated at reflux temperature under a Dean and Stark trap for 20 hr. The distillate was periodically removed and the main bulk of solvent replenished as necessary. Removal of the xylene solvent under reduced pressure afforded a light brown oil which was purified by the addition of 60–80° C. petroleum ether (100 ml) and stirring for 1 hr. The white crystalline product was filtered off, washed with a little petroleum ether and dried in air. The yield of coupler (C21) was 19.5 g, 62%.

|  | Requires: C 69.2%; H 8.1%; N 6.9%<br>Found: C 69.0%; H 7.9%; N 6.9% |
|---|---|

EXAMPLE 3

Preparation of Coupler (C17)

Ethyl N-(2-chloro-4-dodecylsulphonylphenyl)-2-(3-benzyl-2,5-dioxo-1,3-diazolidin-1-yl)malonamate

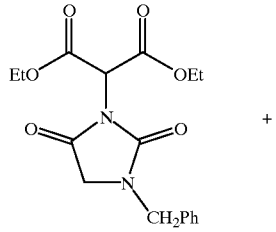

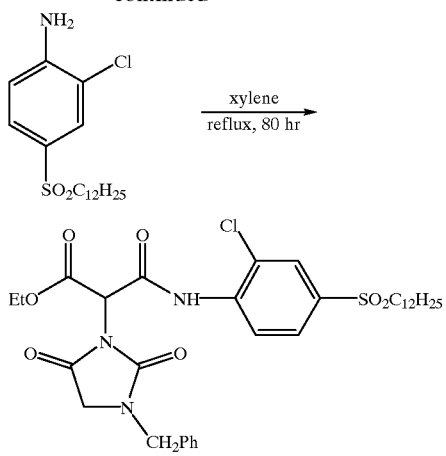

Diethyl 2-(3-benzyl-2,5-dioxo-1,3-diazolidin-1-yl)-malonate (19.3 g, 55.5 mmol) and (4-amino-3-chlorophenyl)dodecylsulphone (20.0 g,56.0 mmol) were added to xylene (100 ml) and refluxed under Dean and Stark conditions for 80 hr, occasionally removing a small amount of distillate and replenishing the solvent as necessary. The reaction was followed by TLC (1:2 ethyl acetate:60–80° C. petroleum ether), the Rf of the product being between that of the two starting materials. The xylene was removed on the rotary evaporator and the residual yellowish oil stirred with 60–80° C. petroleum ether (100 ml), allowed to settle and decanted from the oil. This removed some front-running impurities. On standing the oil solidified to a crystalline mass which was crystallized from toluene and petrol to give a white solid, 17.0 g, 46%.

|  | Requires: C 59.85%; H 6.7%; N 6.35%<br>Found: C 59.6%; H 6.4%; N 6.25% |
|---|---|

EXAMPLE 4

Preparation of Coupler (C1)

Ethyl N-(2-chloro-5-n-dodecyloxycarbonylphenyl)-2-phthalimidomalonamate

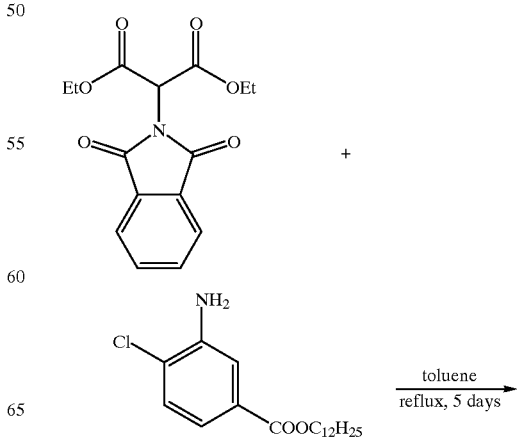

-continued

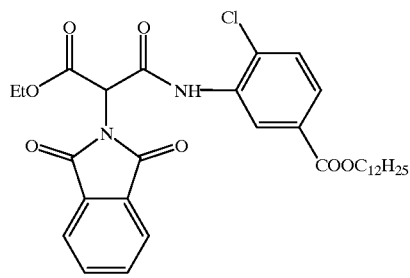

Diethyl 2-phthalimidomalonate (15.26 g, 50.0 mmol) and n-dodecyl 3-amino-4-chlorobenzoate (16.99 g, 50.0 mmol) were added to toluene (300 ml) and refluxed under Dean and Stark conditions for 5 days, occasionally removing a small amount of distillate and replenishing the solvent as necessary. The reaction was followed by TLC (1:2 ethyl acetate:60–80° C. petroleum ether), the Rf of the product being between that of the two starting materials. The toluene was removed on the rotary evaporator and on standing the viscous oil solidified. Crystallization from 60–80° C. petroleum ether gave a white solid, 13.92 g, 47%

| $C_{32}H_{39}ClN_2O_7$ | Requires: C 64.2%; H 6.6%; N 4.7% |
| | Found: C 64.4%; H 6.5%; N 4.7% |

EXAMPLE 5

Preparation of Coupler (C34)

Ethyl N-(2-chloro-5-n-hexadecylsuphamoylphenyl)-2-phthailimidomalonamate

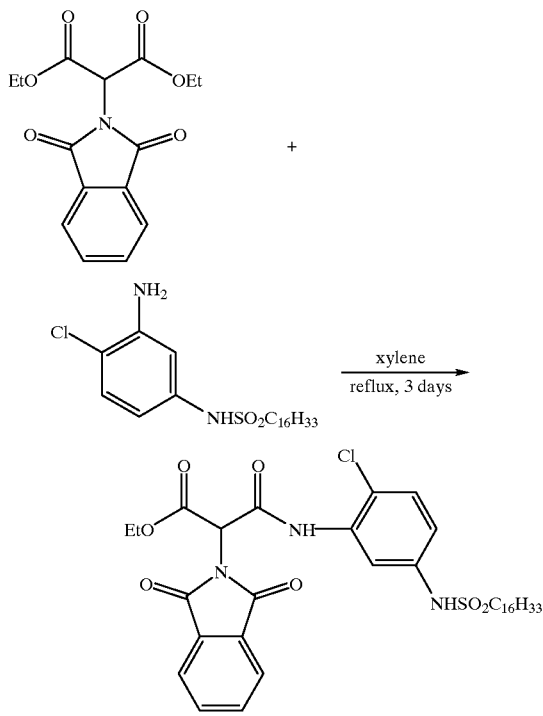

Diethyl 2-phthalimidomalonate (10.0 g, 32.8 mmol) and N-(3-amino-4-chlorophenyl)hexadecylsulphonamide (14.0 g, 32.5 mmol) were added to xylene (300 ml) and refluxed under Dean and Stark conditions for 3 days, occasionally removing a small amount of distillate and replenishing the solvent as necessary. The reaction was followed by TLC (1:3 ethyl acetate:60–80° C. petroleum ether), the Rf of the product being between that of the two starting materials. The xylene was removed on the rotary evaporator and the residue purified by column chromatography using 1:3 ethyl acetate:60–80° C. petroleum ether at first and then 1:2 ethyl acetate:60–80° C. petroleum ether. The product fraction was crystallized from petroleum ether to give a very fine solid which was difficult to filter. The solid was dried in air and ground to a light powder, 11.6 g, 52%.

Couplers C25, C31 and C32 were prepared similarly in yields of 62%, 56% and 56% respectively.

PHOTOGRAPHIC EVALUATION OF YELLOW COUPLERS

The yellow couplers of the present invention (and control compounds) were dispersed in coupler solvent and incorporated into photographic coatings containing a silver bromoiodide emulsion, on a transparent support, according to the following coating diagram:

| Gel Supercoat | Gelatin | 1.50 gm$^{-2}$ |
|---|---|---|
| Emulsion Layer | Silver bromoiodide | 0.81 gm$^{-2}$ |
| | Coupler | 1.932 mmolm$^{-2}$ |
| | Gelatin | 2.42 gm$^{-2}$ |
| | Bis(vinylsulfonyl)methane (hardener) | 0.06 gm$^{-2}$ |
| Support | Cellulose acetate | |

Aqueous dispersions of the yellow couplers were prepared by methods known in the art. The dye-forming coupler dispersions contained 6% by weight of gelatin, 9% by weight of coupler and a 1.0:0.5:1.5 weight ratio of coupler to di-n-butyl phthalate coupler solvent to cyclohexanone auxiliary solvent. The auxiliary solvent was included to aid in dispersion preparation and was removed by washing the dispersion for 6 hours at 4° C. and pH 6.0.

(i) Sensitometric testing

The experimental photographic coatings prepared in this way were slit and chopped into 30 cm×35 mm test strips. After hardening the strips were exposed (1.0 sec) through a 0–4.0 neutral density step wedge (0.2 ND step increments) and Daylight V. Wratten 35+38A filters and 0.3 ND filter then processed through a standard C-41 process as described in the British Journal of Photography Annual (1988) 196–198 using the following steps and process times:

| Developer | 2.5 minutes |
|---|---|
| Bleach | 4.0 minutes |
| Wash | 2.0 minutes |
| Fix | 4.0 minutes |
| Wash | 2.0 minutes |

For each test strip, Status M densities were measured as a function of exposure using a spectral array automatic transmission densitometer. Measurements of sensitometric parameters—minimum density (Dmin), maximum density (Dmax) and contrast (γ)—were obtained from plots of density vs. log exposure (DlogE curves).

(ii) Spectrophotometric testing 35 mm Test strips were exposed as above through a 0–0.9 ND step-wedge (0.3 ND increments) and Daylight V, Wratten 35+38A filters and the correct ND filters to give an optical density of about 1.0. The strips were processed using the standard conditions described above and samples cut from the yellow dye image step with density closest to 1.0. Visible absorption spectra of the resultant yellow dyes (normalized to 1.0 density) were obtained using a Pye-Unicam SP8-100 spectrophotometer. Dye hues are expressed in terms of the wavelength corresponding to the maximum absorption peak ($\lambda_{max}$) and the width of the curve at half the peak height—known as the half-bandwidth (HBW).

The results of the testing described above are set out in the following Tables 1 and 2:

TABLE 1

| | Sensitometric Data | | |
|---|---|---|---|
| COUPLER | Dmin | Dmax | γ |
| Coupler C16 | 0.15 | 2.25 | 2.45 |
| Control CC1 | 0.14 | 2.54 | 1.99 |
| Control CC2 | 0.12 | 2.24 | 1.63 |

TABLE 2

| | Spectrophotometric Data | |
|---|---|---|
| COUPLER | γmax (nm) | HBW (NM) |
| Coupler C3 | 447.0 | 82.0 |
| Control CC1 | 446.5 | 95.5 |
| Control CC2 | 449.0 | 89.5 |

From Table 1 it can be seen that coupler C16 has good $D_{max}$ and contrast γ. By comparison Control CC1 has better $D_{max}$ but inadequate contrast, and Control CC2 has similar $D_{max}$ but much lower contrast.

Table 2 shows that the half-band width for coupler C3 is much narrower than for both the control couplers, which is better for color reproduction, there being less unwanted absorptions.

The couplers can be seen therefore to provide a useful range of activity and dye hue.

What is claimed is:

1. A method of synthesis of a image-dye forming coupler of formula (I)

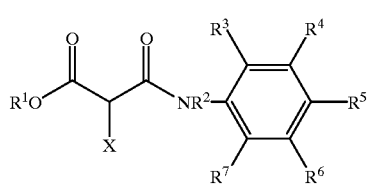

(I)

wherein X is a substituent linked to the coupler by an atom of oxygen, sulfur or nitrogen $R^1$ is an alkyl or aryl group, $R^2$ is a hydrogen atom or an alkyl group; $R^3$ to $R^7$ are the same or different and selected from a hydrogen atom and substituent groups;

which method comprises the reaction of a compound of formula (II)

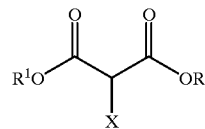

(II)

wherein R and $R^1$ are the same or different and are as defined above for $R^1$ and X is as defined above with a compound of formula (III)

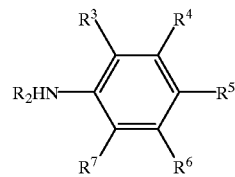

(III)

wherein $R^2$ to $R^7$ are as defined above, in the presence of an inert organic solvent.

2. A method according to claim 1 wherein the solvent is a non-aprotic solvent selected from a hydrocarbon and a high-boiling ether.

3. A method according to claim 2 wherein the solvent is toluene or xylene.

4. A method according to claim 1 wherein the reaction is carried out at the boiling point of the solvent.

5. A method according to claim 1 wherein the compound of formula (II) is prepared by reaction of a compound of formula (IV)

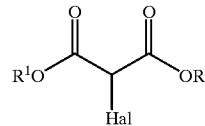

(IV)

wherein R and $R^1$ are as defined in claim 1 and Hal is a halogen atom, with a compound of formula XH, where X is as defined in claim 1, in a solvent in the presence of a base.

6. A method according to claim 5 wherein the solvent is acetonitrile.

7. A method according to claim 5 wherein the base is tetramethylguanidine.

8. A method according to claim 5 wherein the reaction is carried out in the range 0–100°.

9. A method according to claim 8 wherein the reaction is carried out at room temperature.

10. A method according to claim 1 wherein at least one of the groups $R^1$ to $R^7$ contains a photographic ballast group.

11. A method according to claim 1 wherein $R^1$ is an unsubstituted or substituted alkyl, phenyl, naphthyl or pyridyl group.

12. A method according to claim 11 wherein $R^1$ is an alkyl group.

13. A method according to claim 1 wherein $R^2$ is a hydrogen atom.

14. A method according to claim 1 wherein $R^3$ to $R^7$ are independently is selected from H, halogen, $R^1$, $R^1O$, $R^1_2N$, $R^1HN$, $H_2N$, $R^1S$, $R^1SO$, $R^1SO_2NH$, $R^1SO_2$, $R^1SO_2O$, $R^1OOC$, HOOC, $R^1COO$, $R^1NHCO$, $R^1_2NCO$, $R^1NHCONH$, $R^1CONH$ $R^1NHSO_2$, $R^1_2NSO_2$, $H_2NSO_2$, $R^1CO$, $NO_2$, CN, $CF_3$, $P(OR^1)_3$ and $PO(OR^1)_3$ groups, wherein $R^1$ is as defined in claim 1.

15. A method according to claim 14 wherein a non-hydrogen $R^3$ to $R^7$ is in an ortho position in the phenyl ring.

16. A method according to claim 14 wherein $R^3$ and $R^4$, $R^4$ and $R^5$, $R^5$ and $R^6$ and/or $R^6$ and $R^7$ represent fused cyclic groups.

17. A method according to claim 1 wherein X is selected from acyloxy, sulfonyloxy, aryloxy, phosphonyloxy, azo groups, sulphonamides, heteroaryloxy, alkylthio, arylthio, heteroarylthio and n-heterocycles (attached to the coupling site by the heteroatom), such as urethane, imido, 2,4-oxazolidinedione, pyridone, pyridazone, phthalimido, succinimido, hydantoinyl, triazole, triazoledione, tetrazole, imidazole, pyrazole and benzotriazole groups.

\* \* \* \* \*